US011589807B2

(12) United States Patent
Liu

(10) Patent No.: US 11,589,807 B2
(45) Date of Patent: Feb. 28, 2023

(54) BIOSENSOR FOR MONITORING EYEDROP USAGE COMPLIANCE

(71) Applicant: THE REGENTS OF THE UNIVERSITY OF CALIFORNIA, Oakland, CA (US)

(72) Inventor: John Liu, San Diego, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 63 days.

(21) Appl. No.: 16/611,462

(22) PCT Filed: May 11, 2018

(86) PCT No.: PCT/US2018/032402
§ 371 (c)(1),
(2) Date: Nov. 6, 2019

(87) PCT Pub. No.: WO2018/209289
PCT Pub. Date: Nov. 15, 2018

(65) Prior Publication Data
US 2020/0138367 A1 May 7, 2020

Related U.S. Application Data

(60) Provisional application No. 62/504,717, filed on May 11, 2017.

(51) Int. Cl.
*G16H 40/67* (2018.01)
*G16H 20/13* (2018.01)
(Continued)

(52) U.S. Cl.
CPC .......... *A61B 5/4833* (2013.01); *A61B 5/0008* (2013.01); *A61B 5/0022* (2013.01);
(Continued)

(58) Field of Classification Search
CPC ................ A61B 5/4833; A61B 5/0008; A61B 5/0022; A61B 5/14532; A61B 5/6821;
(Continued)

(56) References Cited

U.S. PATENT DOCUMENTS

| | | | |
|---|---|---|---|
| 6,647,133 B1 | 11/2003 | Morita | |
| 2003/0139687 A1 | 7/2003 | Abreu | |
| 2006/0229502 A1* | 10/2006 | Pollock | A61B 5/14532 600/300 |

(Continued)

OTHER PUBLICATIONS

International Search Report and Written Opinion in PCT/US2018/032402 dated Aug. 1, 2018.
International Preliminary Report on Patentability in PCT/US18/32402, dated Nov. 12, 2019.

*Primary Examiner* — Patrick Fernandes
*Assistant Examiner* — Liam A Wallace
(74) *Attorney, Agent, or Firm* — Sheppard, Mullin, Richter & Hampton LLP

(57) ABSTRACT

Systems and methods for monitoring eyedrop usage are disclosed. Example embodiments include a system to monitor eyedrop usage. The system may include a detection and activation circuit couplable to a wireless biosensor and an eyedrop dispenser. The detection and activation circuit may include a pressure transducer that transmits a signal upon detecting a force at, or above, a threshold value. The system may also include a wireless biosensor insertable into a region of an eyelid. The wireless biosensor may include a sensor to detect the physical change and the chemical change of tears as a result of eyedrop usage. The wireless biosensor may also include a transceiver to receive the signal that activates the sensor for an activation time.

20 Claims, 6 Drawing Sheets

(51) Int. Cl.
   *A61B 5/00*      (2006.01)
   *A61B 5/145*     (2006.01)
   *A61F 9/00*      (2006.01)

(52) U.S. Cl.
   CPC ........ *A61B 5/14532* (2013.01); *A61B 5/6821* (2013.01); *A61F 9/0008* (2013.01); *G16H 20/13* (2018.01); *G16H 40/67* (2018.01); *A61B 2562/0247* (2013.01); *A61B 2562/0271* (2013.01)

(58) Field of Classification Search
   CPC .... A61B 2562/0247; A61B 2562/0271; G16H 20/13; G16H 40/67; A61F 9/0008
   See application file for complete search history.

(56) References Cited

U.S. PATENT DOCUMENTS

| | | | |
|---|---|---|---|
| 2009/0099626 A1 | 4/2009 | De Juan | |
| 2010/0034870 A1* | 2/2010 | Sim | A61K 9/0051 424/427 |
| 2012/0245444 A1 | 9/2012 | Otis | |
| 2014/0228783 A1 | 8/2014 | Kraft | |
| 2015/0359667 A1* | 12/2015 | Brue | H04L 67/12 604/295 |
| 2016/0003760 A1* | 1/2016 | Etzkorn | A61B 5/6821 205/122 |
| 2016/0071423 A1* | 3/2016 | Sales | A61B 5/4076 434/127 |
| 2017/0046501 A1* | 2/2017 | Coleman | G16H 20/13 |
| 2018/0193193 A1* | 7/2018 | Kahook | A61B 5/4839 |

\* cited by examiner

BIOSENSOR FOR MONITORING EYEDROP USAGE COMPLIANCE

RELATED APPLICATIONS

This application is a U.S. National Phase under 35 U.S.C. § 371 of International Application No. PCT/US US2018/032402, filed on May 11, 2018, which claims the benefit of U.S. Provisional Patent Application No. 62/504,717, filed on May 6, 2017, the content of which is incorporated herein by reference in its entirety.

TECHNICAL FIELD

The present disclosure is generally related to a wireless biosensor. In particular, embodiments of the present disclosure provide a system including a wireless biosensor for monitoring periodic (e.g., daily) eyedrop usage.

DESCRIPTION OF THE RELATED ART

Eyedrops are often used to treat various eye-related medical problems. However, it is estimated that one third of the patient population requiring eyedrops fails to comply with eyedrop dosage instructions. As a result, there is a need to track and monitor a patient's eye environment to determine whether or not the patient has been correctly adhering to his or her eyedrop usage requirements. By doing so, this may lead to better eye health maintenance.

Additionally, it may also be useful to monitor the patient's eye environment for certain physical and chemical indicators, such as temperature and glucose measurements. While there are contact lenses that can be placed on the surface of an eye to measure certain physical and chemical measurements, contact lenses may often blur a patient's field of view. Additionally, contact lenses may even bring great discomfort to the user, especially for patients who have never worn contact lenses.

BRIEF SUMMARY OF EMBODIMENTS

The disclosed technology relates generally to monitoring eyedrop usage, and more particularly, several embodiments relate to systems and methods for monitoring eyedrop usage using a wireless biosensor.

In accordance with aspects of the present disclosure, a server system monitors eyedrop usage. The system includes a detection and activation circuit couplable to a wireless biosensor and an eyedrop dispenser. The detection and activation circuit includes a pressure transducer detecting a force applied to the pressure transducer. The pressure transducer transmits a signal upon detecting a force at, or above, a threshold value. The system includes a wireless biosensor insertable into a region of an eyelid. The wireless biosensor includes a sensor to detect the physical change and the chemical change to tears as a result of eyedrop usage from the eyedrop dispenser when activated. When the eyedrop dispenser is activated, it sends a signal to the wireless biosensor. The wireless biosensor includes a transceiver to receive the signal. Receiving the signal activates the wireless biosensor for an activation time. The wireless biosensor deactivates after the activation time.

In embodiments, the region of the eyelid includes a lower lacrimal punctum of the eyelid.

In embodiments, the sensor includes a temperature sensor to detect a change in a temperature to the tears as a result of the eyedrop usage during the activation time.

In embodiments, the detection and activation circuit is couplable to a surface of the eyedrop dispenser using an adhesive side of the detection and activation circuit.

In embodiments, the detection and activation circuit includes a hydrogel material couplable to different types of eyedrop dispensers.

In embodiments, the detection and activation circuit includes a temperature sensor to be thermally coupled to a surface of the eyedrop dispenser. The detection and activation circuit includes a fingerprint identification sensor to detect a user's fingerprint to identify which user is using the eyedrop dispenser.

In embodiments, the activation time includes a duration of about five minutes.

In embodiments, the system further includes a display device including a display. Information indicating the physical change and the chemical change are displayed on the display.

In embodiments, the physical change includes a change in temperature to the tears as a result of the eyedrop usage during the activation time.

Additional aspects of the present disclosure relate to a method. The method includes coupling a detection and activation circuit to a wireless biosensor and to an eyedrop dispenser. The detection and activation circuit includes a pressure transducer detecting a force applied to the pressure transducer. The pressure transducer transmits a signal upon detecting a force at, or above, a threshold value. The method further includes inserting a wireless biosensor into an eyelid. The wireless biosensor includes a sensor to detect the physical change and the chemical change to tears as a result of eyedrop usage from the eyedrop dispenser when activated. The wireless biosensor includes a transceiver to receive the signal to activate the wireless biosensor for an activation time. The method further includes detecting the force at, or above, the threshold value using the pressure transducer. The method further includes activating the wireless biosensor according to the activation time. The method further includes during the activation time, dispensing eyedrops from eyedrop dispenser on a surface of the eye. The method further includes responsive to detecting the force at, or above, the threshold value, detecting the physical change and the chemical change to the tears as a result of eyedrop usage during the activation time.

In embodiments, the region of the eyelid includes a lower lacrimal punctum of the eyelid.

In embodiments, the sensor includes a glucose sensor to detect a change in a glucose concentration of the eye during the activation time.

In embodiments, the detection and activation circuit is couplable to a surface of the eyedrop dispenser using an adhesive side of the detection and activation circuit.

In embodiments, the detection and activation circuit includes a hydrogel material couplable to different types of eyedrop dispensers.

In embodiments, the chemical change includes a change in glucose concentration of the eye during the activation time.

In embodiments, the detection and activation circuit includes a temperature sensor thermally couplable to a surface of the eyedrop dispenser. The detection and activation circuit includes a fingerprint identification sensor to detect a user's fingerprint to identify which user is using the eyedrop dispenser.

In embodiments, the detection and activation circuit activates the wireless sensor based on a force applied to at least a portion of the detection and activation circuit.

In embodiments, the activation time includes a duration of about five minutes.

In embodiments, the method further includes transmitting the information indicating the physical change and the chemical change to a display device, wherein the display device includes a display. The method further includes displaying the information indicating the physical change and the chemical change on the display of the display device.

Additional aspects of the present disclosure relate to a system to monitor eyedrop usage. The system includes a wireless biosensor insertable into a region of an eyelid. The wireless biosensor includes a sensor to detect a physical change and a chemical change to tears as a result of eyedrop usage. The wireless biosensor is activated for an activation time by a signal and deactivated after the activation time. The wireless biosensor includes a transceiver to receive a signal from an external detection and activation circuit. The external detection and activation circuit, coupled to an eyedrop dispenser, transmits the signal to the wireless biosensor when a force at, or above, a threshold is applied to the external detection and activation circuit.

BRIEF DESCRIPTION OF THE DRAWINGS

Various embodiments are disclosed herein and described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

The details of some exemplary embodiments of the methods and systems of the present disclosure are set forth in the description below. Other features, objects, and advantages of the disclosure will be apparent to one of skill in the art upon examination of the following description, drawings, examples and claims.

Various embodiments of the present disclosure relate to a system for monitoring periodic (e.g., daily) eyedrop usage. By way of example only, the system may include a wireless biosensor configured to be inserted into the eyelid (e.g., into a lacrimal puncta of the eye) by a medical professional. The biosensor may be configured to accurately measure physical and chemical properties of the patient's eye and surrounding tissue, such as temperature and glucose concentration levels, and the change in these properties after eyedrops are used.

Additionally, the system may also include a detection and activation circuit that is used as part of, or in conjunction with, an eyedrop dispenser that can be used to detect dispensing of eyedrops. In some embodiments, the detection and activation circuit can be configured to not only sense a dispensing operation, but also send additional dispensing parameters such as, for example, dispensed volume, time of dispensing, temperature of the eyedrops dispensed, and so on. The detection and activation circuit may include various sensors, such as a fingerprint identification sensor, a temperature sensor, and a pressure sensor. The detection and activation circuit may also include a clock, a timer, a communications transmitter or transceiver, or other components. In some embodiments, the detection and activation circuit may communicate with the biosensor (e.g., wirelessly) to perform functions such as, for example, activating or controlling the biosensor and receiving, storing information collected by the biosensor. This may allow for the real-time monitoring of the patient's eye condition while the biosensor is turned on and in use. In some implementations, the eyedrop dispenser can be configured to include the detection and activation circuit components as an integrated package. In other implementations, the detection and activation circuit may be configured as an add-on detection and activation circuit that can be fitted to an existing eyedrop dispenser.

Figure 1:
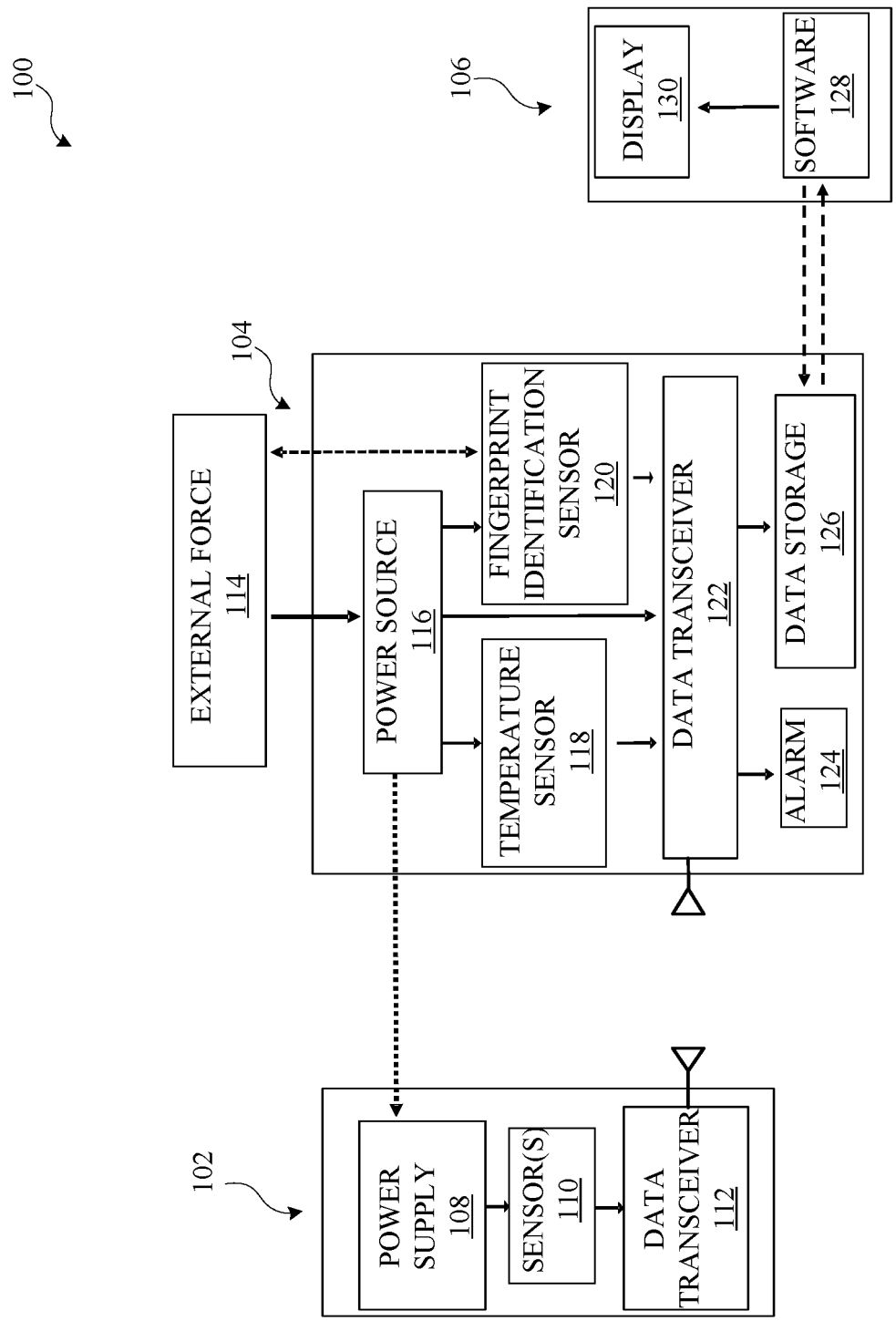
FIG. 1 illustrates a system for monitoring daily eyedrop usage according to one embodiment of the present disclosure.

FIG. 1 illustrates an example system 100 for monitoring periodic eyedrop usage according to one embodiment of the present disclosure. As depicted, the system 100 may include detection and activation circuit 104 to be placed over any eyedrop dispenser. The system 100 may also include a biosensor 102 and an electronic display 106.

In this example, biosensor 102 includes power supply 108, sensors 110, and data transceiver 112. Biosensor 102 may detect physical and chemical properties of the eye. The physical properties of the eye may include, for example, temperature changes, pressure changes, blinking occurrences, or other physical properties. The chemical properties may include, for example, glucose concentration changes, salinity concentrations, pH levels, or other chemical properties.

Figure 4:
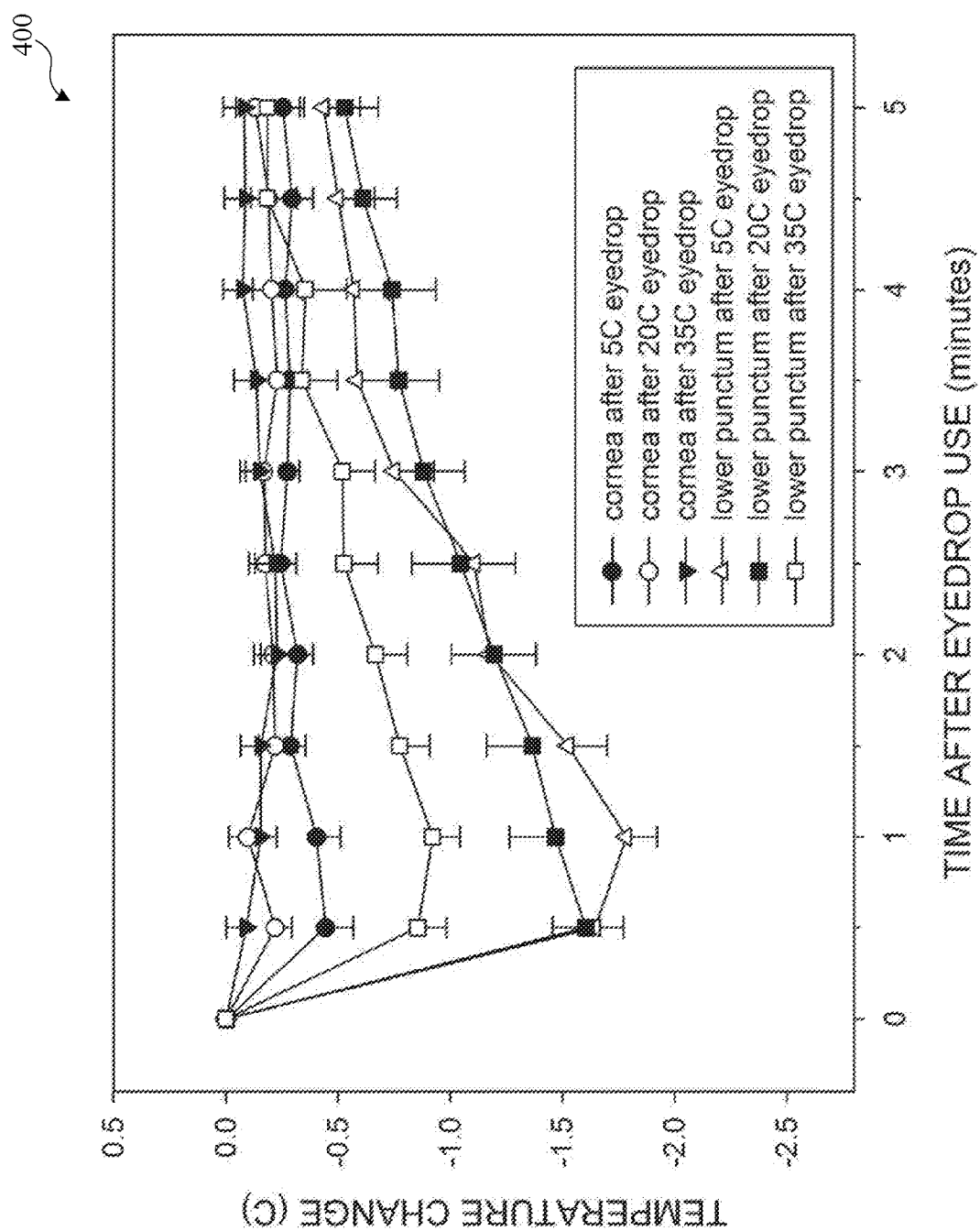
FIG. 4 illustrates temperature changes to different parts of the eye using eyedrops stored at different temperatures, according to one embodiment of the present disclosure.

Biosensor 102 may be inserted or applied at various locations in, or near, the eye to measure the physical and chemical properties of the eye's response to the application of eyedrops. In some embodiments, biosensor 102 may be inserted into the lower lacrimal punctum. This insertion location may be desirable because this location is generally more sensitive to changes in temperature than other locations on the eye. For example, as illustrated in FIG. 4, the lower punctum area, as noted by the white triangle, black square, and white square, shows a larger temperature change in response to an eyedrop application as compared to the cornea. The change in temperature for the lower punctum one minute after eyedrop application is about 1 to about 1.75 degrees Celsius. On the other hand, the change in temperature of the cornea is no greater than about 0.5 degrees Celsius at the same time. As this example illustrates, the lower level of responsiveness to the application of the eyedrops could lead to false negatives in reporting.

Power supply 108 may be charged wirelessly, and powered on and powered off, or activated and deactivated, wirelessly. In embodiments, power supply 108 may include a rechargeable battery, capacitive storage device or other power storage element. In some embodiments, the rechargeable battery may be recharged using inductive charging. Inductive charging may include using an induction coil to generate alternating electromagnetic fields from a charger base. A second induction coil may be placed in biosensor 102 to receive power from the alternating electromagnetic fields and convert it into electric current to charge the rechargeable battery. Biosensor 102 may charge within a certain distance to the charging base. Biosensor 102 may be chargeable while inserted into the eyelid. In some embodiments, a battery charge may coincide with regular appointments with a medical professional, or biosensor 102 otherwise be removed for charging via wired or wireless means. In other embodiments, the battery may not be rechargeable.

In some embodiments, the rechargeable battery may be recharged using radio frequency. Electromagnetic waves may be transmitted by a charging station and receivers on biosensor 102 may receive the electromagnetic waves and convert the electromagnetic waves into a charging current. A person of ordinary skill in the art will recognize other forms of wireless charging may be used.

Furthermore, biosensor 102 may also include various sensors 110 configured to detect and measure the physical and chemical properties of its environment. Biosensor 102 may be configured to be implanted, or inserted, into the lower lacrimal punctum of an eyelid. The lower lacrimal punctum may function to collect tears produced by the lacrimal glands. The lower lacrimal punctum may open into a tube called the lacrimal canaliculus. The lacrimal canaliculus joins puncta to the lacrimal sac. This system allows excess tears to drain from the eye into the nose.

Biosensor 102 may include sensors 110 that are capable of taking the local temperature and tear glucose concentration. In some embodiments, the temperature sensor may be in contact with an inner edge of biosensor 102. In embodiments, the temperature sensor may not contact an inside edge or an outside edge of biosensor 102. In other words, the temperature sensor may be enveloped by biosensor 102. A first temperature may be used as a baseline. When the power is activated, a graph of the temperature changes may be sent to detection and activation circuit 104. One of sensors 110 may generate a change between a first glucose level and a second glucose level. The change may be displayed on electronic display 106. Other sensors 110 detecting physical changes may not need to be in contact within the inner edge of biosensor 102. In embodiments, sensors 110 detecting chemical changes may need to be in contact with the inner edge to detect chemical changes, such as changes in tear glucose concentration.

Other additional sensors 110 may be incorporated into biosensor 102, which may include, for example, pressure sensors, motion sensors, pH sensors, salinity sensors, osmolarity sensors, and the like. Pressure sensors may be used to detect the change in pressure as a tear is introduced into biosensor 102. Motion sensors may be used to detect the number of times eyelids close and open, particularly after eyedrop usage. In embodiments, pH sensors may be used to detect pH levels of tears, and the changes in pH based on eyedrop usage. Salinity sensors may be used to detect a concentration of dissolved salts in tears, and the changes in concentration based on eyedrop usage. Osmolarity sensors may be used to detect the concentration of other solutes, especially during eyedrop usage. As such, a wide variety of sensors 110 appreciated by one of ordinary skill in the art may be incorporated into biosensor 102.

By way of further example only, biosensor 102 may also include data transceiver 112, which may wirelessly transmit the data that sensors 110 have collected and measured. Using various radiofrequency identification (RFID) or micro-electromechanical systems (MEMS), biosensor 102 may communicate wirelessly with a power source 116 and data transceiver 122. Data transceiver 112 may receive signals from detection and activation circuit 104 to "wake up" sensors 110 or other components of biosensor 102. A person of ordinary skill in the art will understand that other wireless communications may be used, such as communications networks (e.g., via the Internet), or other communications interfaces.

In some embodiments, biosensor 102 may be cylindrical, round, or other shapes. Biosensor 102 may be made out of silicone, polymers, or other materials. In embodiments, biosensor 102 may be shaped for insertion into a desired portion of the eyes, such as the lower lacrimal punctum. A center of biosensor 102 may be configured to receive liquid, such as a tear. One example of such a biosensor is described in more detail in FIGS. 2 and 3 below.

In embodiments, detection and activation circuit 104 may include power source 116, temperature sensor 118, fingerprint identification sensor 120, data transceiver 122, alarm 124, data storage 126, and control circuitry (not shown). The control circuitry may be configured to control and operate the various components of the detection and activation circuit. The control circuitry may include one or more processors. In some embodiments, alarm 124 may include a clock and timer. In some embodiments, power source 116 may be a rechargeable battery, which may be similar to power supply 108. As will be understood to a person of ordinary skill in the art, other power sources may be used.

In embodiments, temperature sensor 118 may detect temperature of a region surrounding detection and activation circuit 104. For example, temperature sensor 118 thermally coupled to an eyedrop dispenser may detect the temperature of the eyedrop dispenser, and the temperature of the eyedrops in the eyedrop dispenser. This may be useful to ensure that medication is kept at an appropriate temperature. This may also be used to better determine how changes in temperature to the eye are related to the temperature of the eyedrop dispenser.

In some embodiments, fingerprint identification sensor 120 may detect a fingerprint. Fingerprint identification sensor 120 may capture at least a portion of a fingerprint using a light-sensitive microchip, such as a charge-coupled device (CCD), or a CMOS image sensor to generate a digital image of a fingerprint. As will be understood by a person of ordinary skill in the art, other techniques may be used to detect and capture fingerprints. The fingerprint may be compared against other fingerprints stored, for example, in data storage 126.

In some embodiments, fingerprint identification may be used to identify whether a particular patient or other user is using the eyedrops. In one example, a user may not be the patient. However, the user may be administrating the eyedrops for the patient. Records of who is using the eyedrop dispenser may be helpful for insurance purposes. Fingerprint identification sensor 120 may provide added security for eyedrop usage (e.g., medicated drops), which helps ensure that each patient uses the suggested number of drops over a periodic amount of time.

Data transceiver 122 may be located on detection and activation circuit 104. Data transceiver 122 may be substantially similar to data transceiver 112.

By way of example only, detection and activation circuit 104 may be designed and configured as an add-on that can be fitted to an existing eyedrop dispenser that are sold for commercial use. As such, the detection and activation circuit 104 may be designed to fit a particular eyedrop dispenser, or to universally fit most, if not all, eyedrop dispensers. In embodiments, detection and activation circuit 104 may include hydrogel and the components of detection and activation circuit 104 may be located in the hydrogel. In some embodiments, detection and activation circuit 104 may include gels, silicone, polymers, and other materials. In embodiments, the components of detection and activation circuit 104 may be injected into the hydrogel. Detection and activation circuit 104 may include an adhesive to apply detection and activation circuit 104 as an add-on to eyedrop dispensers.

Additionally, detection and activation circuit 104 may also be configured so that squeezing detection and activation circuit 104 when it is fitted around an eyedrop dispenser, or applying a certain amount of external force 114, or pressure, to detection and activation circuit 104 or a sensor thereof, may send a signal to activate power supply 108 of wireless biosensor 102 according to an activation time. This can be achieved, for example, by including a pressure transducer (not shown) in detection and activation circuit 104 that provides a signal in response to force applied to detection and activation circuit 104. The signal may be sent when external force 114 is at, or above, a threshold value. As such, detection and activation circuit 104 may be configured so that every time the patient applies the eyedrop and squeezes detection and activation circuit 104 placed around the eyedrop dispenser, biosensor 102 becomes activated for an activation time. The activation time may range from about a few seconds to about 1 minute. As another example, the activation time may range from 1 minute to about 15 minutes. In some embodiments, the activation time may be about 5 minutes. In other embodiments, other activation times may be implemented. The actual activation time may be chosen, for example, based on the anticipated period of time in which a reaction or other response to the application of eyedrops is expected to occur.

When activated, sensors 110 may be powered on to detect physical changes and chemical changes. After the activation time, sensors 110 may be powered off. In embodiments, power supply 108 may still power data transceiver 112 of biosensor 102 to receive signals to turn sensors 110 back on. For example, when sensors 110 are powered off, biosensor 102 may be in "sleep" mode." In some embodiments, other components may still be activated during "sleep" mode. When the signal from detection and activation circuit 104 is sent to biosensor 102, biosensor 102 may "wake up."

This configuration may help prevent false positives of changes in physical or chemical properties of the eye. This configuration may also help maintain a long life for biosensor 102 because it is limited to drawing power when activated in such a manner. Once activated, the decrease in local temperature, a dilution of glucose concentration, or any other physical changes and chemical changes may be measured, or detected, by biosensor 102 for the activation time. Next, biosensor 102 may wirelessly transmit the monitored and stored information to data transceiver 122 on detection and activation circuit 104. Data transceiver 122 may send some or all of the measured and received data generated from biosensor 102 to data storage 126 for storage.

In some embodiments, the control circuit on detection and activation circuit 104 may be able to send information collected and monitored by data transceiver 122 to electronic display 106 and alert a patient using alarm 124. This readout may be configured to serve as an alert, such as an audible and/or visual signal. The alert may be configured using alarm 124 when biosensor 102 detects a certain environment that indicates a cause for some concern for the patient, such as decrease in temperature, decrease in glucose level, and/or even increased glucose level with respect to a set value. In further embodiments, other alerts can be generated, such as wireless signals, to transmit an alert to the patient. Alarm 124 may include a clock and timer. Alarm 124 may remind patient of a time of day when eyedrop usage is suggested. For example, a patient may use eyedrops at 9 AM, 12 PM, and 5 PM. Alarm 124 may send an alert every day at these times to the patient.

Additionally, the collected and monitored information may further be transmitted to an electronic display 106, such as a computer, smartphone device or other like devices. Electronic display 106 may include software 128 and display 130. Thus, a medical professional or the patient may be able to view the entire data history measured and stored by biosensor 102. Furthermore, the electronic display 106 may also include software 128 that allows a user to control biosensor 102 and detection and activation circuit 104 from electronic display 106. For example, a medical professional or the patient may be able to configure specific alerts for detection and activation circuit 104 by generating user specific rules and requirements. For example, an alert may be generated to sound off a distinct sound every 5 hours to remind the patient to use his or her eyedrops. In another example, an alert may be generated every time biosensor 102 detects dry eyes or glucose levels above the minimum threshold level.

In some embodiments, the control circuitry may be configured to count the number of times a signal has been sent in a day by the pressure transducer. An alert may be generated if less than a given number of signals are received within a duration of time. For example, consider a scenario in which three eyedrops are suggested every 8 hours, but only two signals have been received by detection and activation circuit 104. Detection and activation circuit 104 may alert the patient at intervals, such as every two hours within the last eight hour period that only two eyedrops have been used. A patient may override this if the actual amount required is less or more than the suggested amount. A patient may silence or dismiss these alerts. Alerts may also be stored in data storage and transmitted to, or later read by, a healthcare professional monitoring usage of the eyedrops by the patient.

In embodiments, data storage 126 may store fingerprint information, temperature information, information gathered from biosensor 102, or other information. Data storage 126 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Data storage 126 may include one or more virtual storage resources (e.g., cloud storage, a virtual private network, and/or other virtual storage resources).

Figure 2:
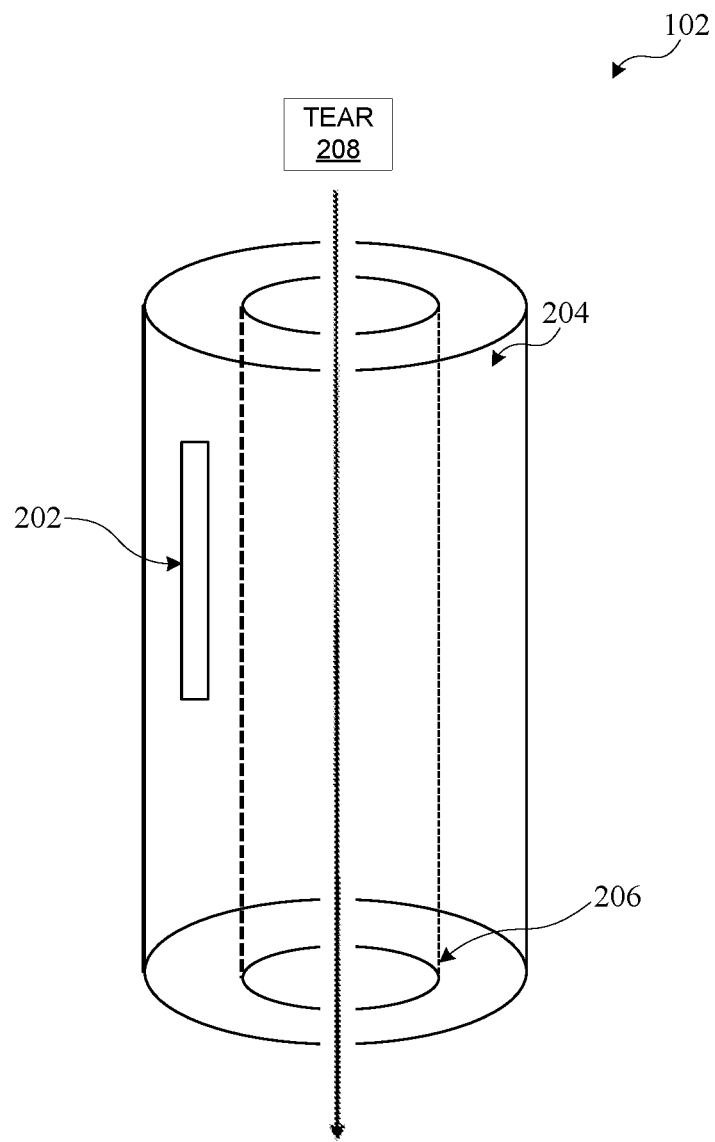
FIG. 2 illustrates a biosensor with a temperature sensor according to one embodiment of the present disclosure.

FIG. 2 illustrates wireless biosensor 102 with temperature sensor 202 according to one embodiment of the present disclosure. By way of example only, biosensor 102 may be a tubular carrier with a diameter of less than about 1 mm. The tubular carrier shape may be configured to be inserted into, or near, the lacrimal punctum of a patient, where biosensor 102 may stay inserted for several weeks. Exterior 204 may be solid and surround hollow center 206 of biosensor 102. Hollow center 206 may be configured to receive tear 208.

After being activated wirelessly via detection and activation circuit 104, biosensor 102 may begin to measure and detect the physical and chemical changes of the patient's eye area. Normally, a tear on the ocular surface has an overall volume of about a few microliters, a temperature of approximately 34-35 degrees Celsius, and a small amount of detectable glucose concentration.

Therefore, upon successful application of an eyedrop solution, the ocular surface of the patient's eye will change its physical and chemical environments as tears are naturally pushed into the lacrimal punctum. As described above, when the eyedrop solution is applied, biosensor 102 may be powered on, or activated, and ready to take the physical and chemical changes of the patient's eye.

As illustrated here, biosensor 102 may include a temperature sensor 202. The temperature sensor 202 may be configured to accurately measure the temperature of the patient's ocular surface near the lacrimal punctum. Temperature sensor 202 may also measure the change in temperature of the tears after eyedrop usage. In certain embodiments, the temperature sensor 202 may not need to be in contact with a patient's natural tears or an eyedrop in order to take the temperature measurements. However, it should be noted that the temperature sensor 202 may still be able to take the temperature measurements even when in contact with a patient's tear or eyedrops.

Figure 3:
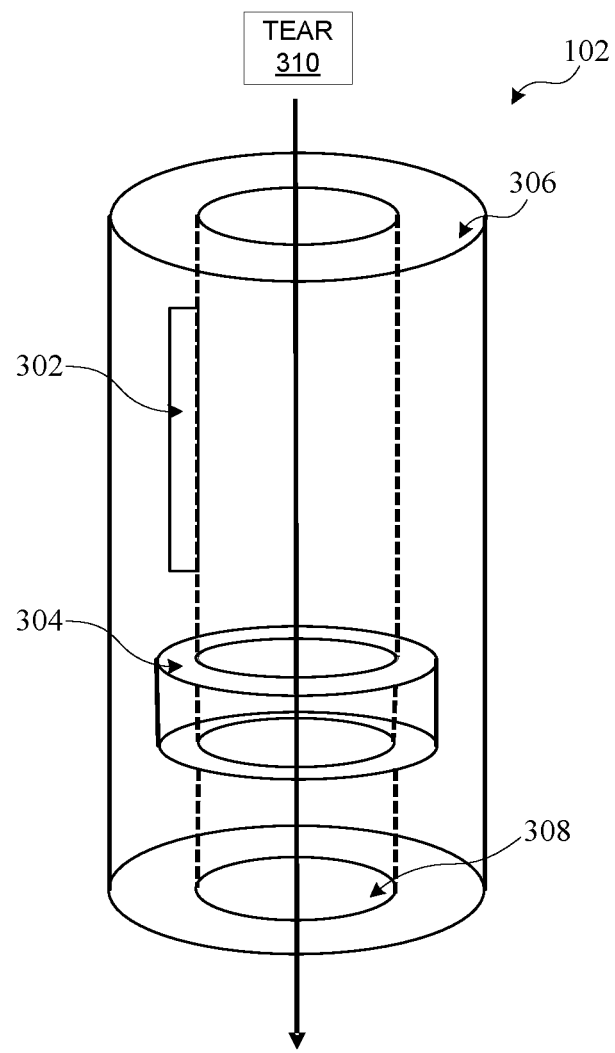
FIG. 3 illustrates a biosensor with a temperature sensor and a glucose sensor according to one embodiment of the present disclosure.

FIG. 3 illustrates wireless biosensor 102 with a temperature sensor 302 and glucose sensor 304 according to one embodiment of the present disclosure. Here, as in FIG. 2, biosensor 102 may be a tubular carrier configured to be implanted onto the lacrimal punctum. However, it should be noted that biosensor 102 need not be limited to a tubular carrier shape, and may be configured to a wide variety of shapes and sizes as appreciated by one of ordinary skill in the art. As illustrated, temperature sensor 302 may be placed against the surface of hollow center 308.

Biosensor 102 may also include a glucose sensor 304. The glucose sensor 304 may detect and measure the glucose concentration from the patient's tear 310, and how the glucose concentration changes after an eyedrop has been applied.

Figure 5:
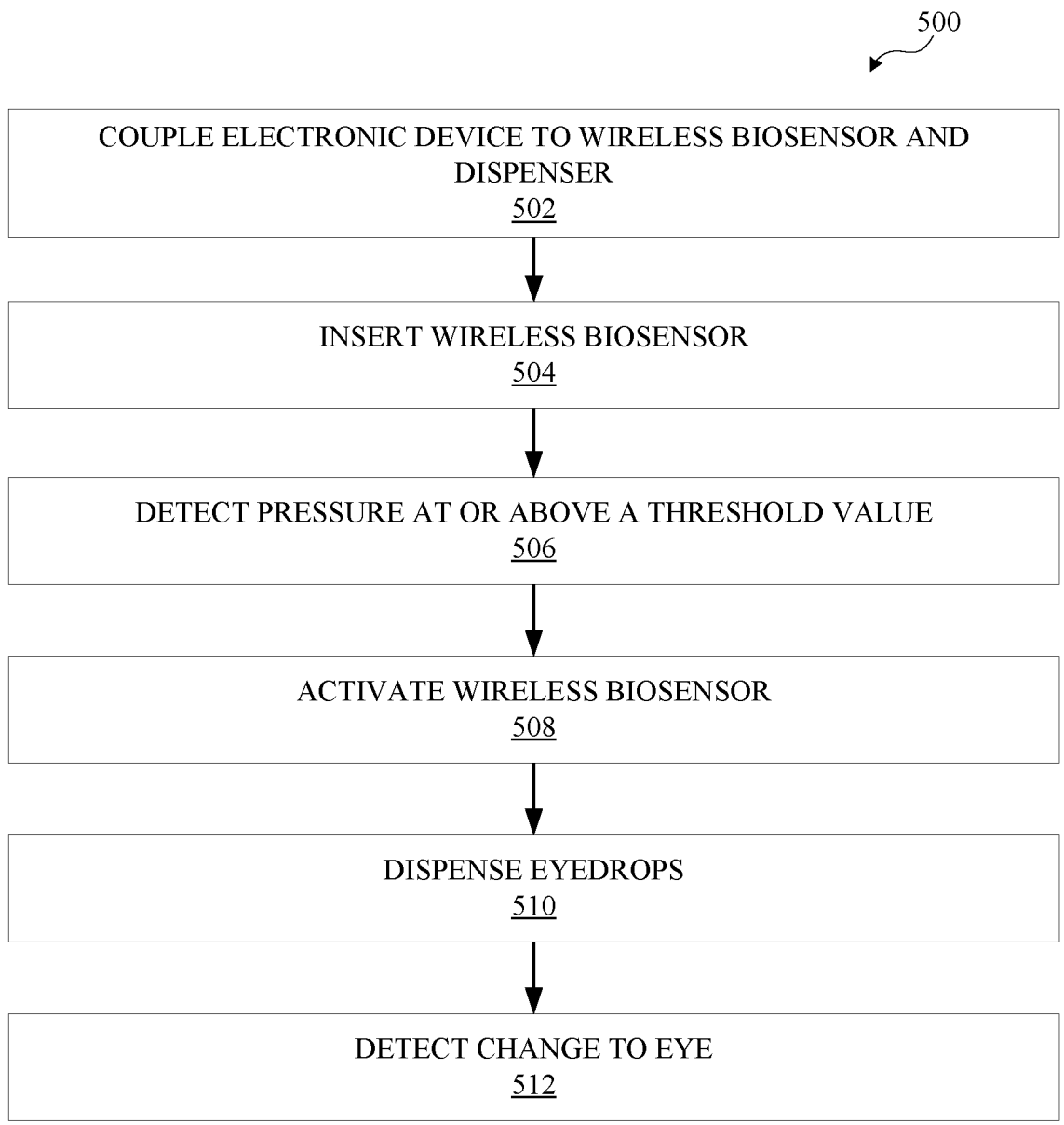
FIG. 5 is an operational flow diagram illustrating an example process for monitoring eyedrop usage, according to one embodiment of the present disclosure.

FIG. 5 is an operation flow diagram illustrating an example process for monitoring eyedrop usage, according to one embodiment of the present disclosure. At operation 502, the detection and activation circuit is coupled to the wireless biosensor and eyedrop dispenser. The detection and activation circuit may be electrically coupled to the wireless biosensor such that the detection and activation circuit and the wireless biosensor can remotely communicate. The detection and activation circuit may be physically coupled to the eyedrop dispenser. The detection and activation circuit may include a pressure transducer capable of detecting a force applied to the pressure transducer. The pressure transducer may send a signal to a biosensor upon detecting a force at, or above, a threshold value.

At operation 504, the wireless biosensor may be inserted into the eyelid. In particular, the wireless biosensor may be inserted into a lower lacrimal punctum. The wireless biosensor may include a sensor to detect a physical change and a chemical change to the tears as a result of eyedrop usage. The sensor may be activated based on a signal. The sensor may be activated for an activation time.

At operation 506, the force may be detected at, or above, a threshold value on the pressure transducer.

At operation 508, as a result of the force sending a signal, the wireless biosensor may be activated for an activation time. In some embodiments, the activation time may be about 5 minutes.

At operation 510, the eyedrops may be dispensed onto a surface of the eye during the activation time. As a result, the tears may physically change and chemically change.

At operation 512, responsive to the signal, the changes to the eye are detected as a result of eyedrop usage. For example, the glucose concentration of the eye may change, the temperature of the eye may change, and the salinity concentration of the tears may change. As described above, the wireless biosensor may be able to detect other changes.

Figure 6:
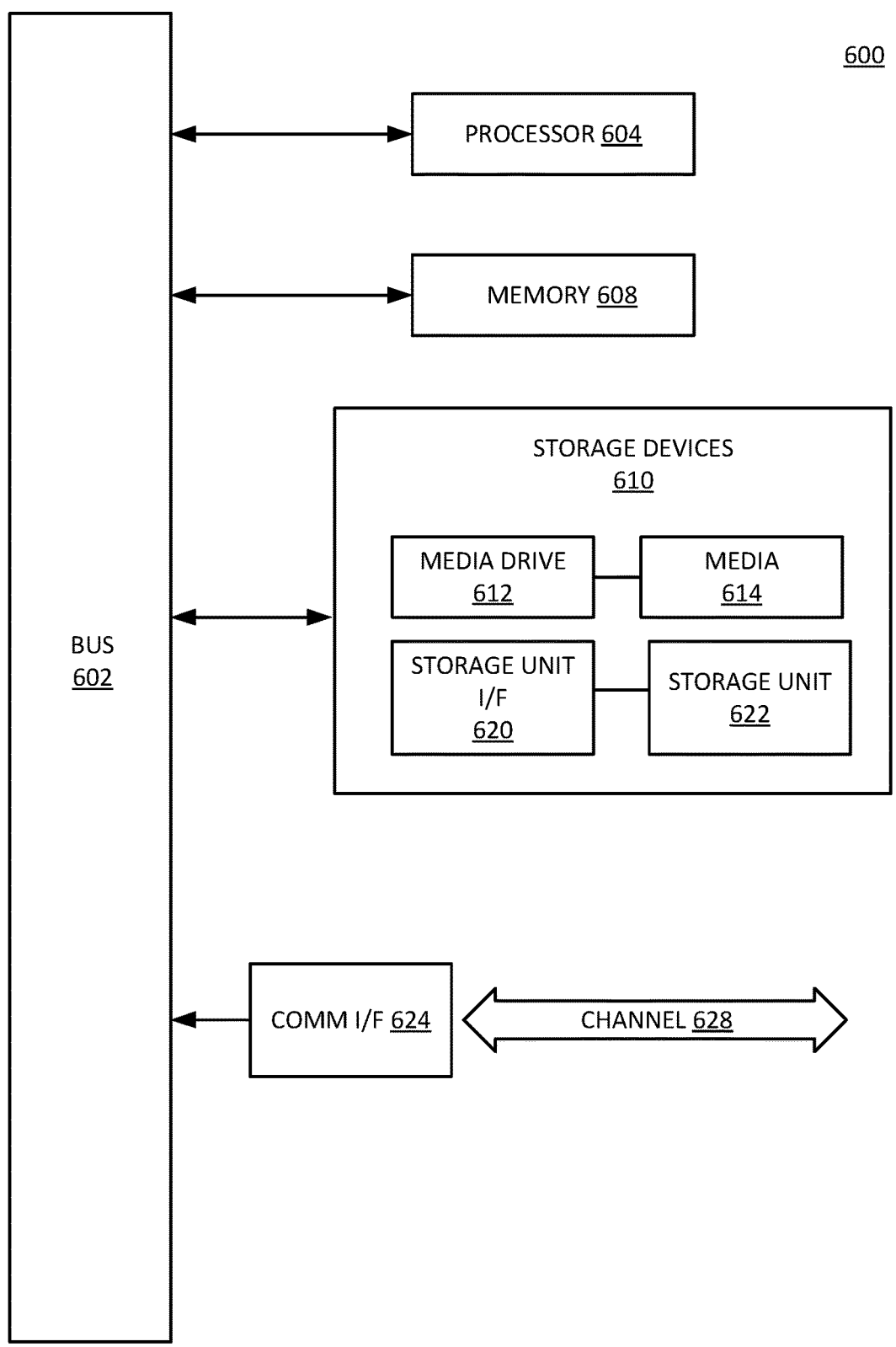
FIG. 6 illustrates an example computing component that may be used in implementing various features of embodiments of the disclosed technology.

As used herein, a circuit might be implemented utilizing any form of hardware, software, or a combination thereof. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. In other words, as would be apparent to one of ordinary skill in the art after reading this description, the various features and functionality described herein may be implemented in any given application and can be implemented in one or more separate or shared circuits in various combinations and permutations. Even though various features or elements of functionality may be individually described or claimed as separate circuits, one of ordinary skill in the art will understand that these features and functionality can be shared among one or more common circuits, and such description shall not require or imply that separate circuits are required to implement such features or functionality.

Where circuits are implemented in whole or in part using software, in one embodiment, these software elements can be implemented to operate with a computing or processing system capable of carrying out the functionality described with respect thereto. One such example computing system is shown in FIG. 6. Various embodiments are described in terms of this example-computing system 600. After reading this description, it will become apparent to a person skilled in the relevant art how to implement the technology using other computing systems or architectures.

Referring now to FIG. 6, computing system 600 may represent, for example, computing or processing capabilities found within desktop, laptop and notebook computers; hand-held computing devices (smart phones, cell phones, palmtops, tablets, etc.); mainframes, supercomputers, workstations or servers; or any other type of special-purpose or general-purpose computing devices as may be desirable or appropriate for a given application or environment. Computing system 600 might also represent computing capabilities embedded within or otherwise available to a given device. For example, a computing system might be found in other detection and activation circuits such as, for example, digital cameras, navigation systems, cellular telephones, portable computing devices, modems, routers, WAPs, terminals and other detection and activation circuits that might include some form of processing capability.

Computing system 600 might include, for example, one or more processors, controllers, control components, or other processing devices, such as a processor 604. Processor 604 might be implemented using a general-purpose or special-purpose processing engine such as, for example, a microprocessor (whether single-, dual- or multi-core processor), signal processor, graphics processor (e.g., GPU) controller, or other control logic. In the illustrated example, processor 604 is connected to a bus 602, although any communication medium can be used to facilitate interaction with other components of computing system 600 or to communicate externally.

Computing system 600 might also include one or more memory components, simply referred to herein as main memory 608. For example, in some embodiments random access memory (RAM) or other dynamic memory, might be used for storing information and instructions to be executed by processor 604. Main memory 608 might also be used for storing temporary variables or other intermediate information during execution of instructions to be executed by processor 604. Computing system 600 might likewise include a read only memory ("ROM") or other static storage device coupled to bus 602 for storing static information and instructions for processor 604.

The computing system 600 might also include one or more various forms of information storage mechanism 610, which might include, for example, a media drive 612 and a storage unit interface 620. The media drive 612 might include a drive or other mechanism to support fixed or removable storage media 614. For example, a hard disk drive, a floppy disk drive, a magnetic tape drive, an optical disk drive, a CD or DVD drive (R or RW), a flash drive, or other removable or fixed media drive might be provided, SQL/NOSQL data bases, and/or other data systems. Accordingly, storage media 614 might include, for example, a hard disk, a floppy disk, magnetic tape, cartridge, optical disk, a CD or DVD, or other fixed or removable medium that is read by, written to or accessed by media drive 612. As these examples illustrate, the storage media 614 can include a computer usable storage medium having stored therein computer software or data.

In alternative embodiments, information storage mechanism 610 might include other similar instrumentalities for allowing computer programs or other instructions or data to be loaded into computing system 600. Such instrumentalities might include, for example, a fixed or removable storage unit 622 and an interface 620. Examples of such storage units 622 and interfaces 620 can include a program cartridge and cartridge interface, a removable memory (for example, a flash memory or other removable memory component) and memory slot, a flash drive and associated slot (for example, a USB drive), a PCMCIA slot and card, and other fixed or removable storage units 622 and interfaces 620 that allow software and data to be transferred from the storage unit 622 to computing system 600.

Computing system 600 might also include a communications interface 624. Communications interface 624 might be used to allow software and data to be transferred between computing system 600 and external devices. Examples of communications interface 624 might include a modem or softmodem, a network interface (such as an Ethernet, network interface card, WiMedia, IEEE 802.XX, Bluetooth® or other interface), a communications port (such as for example, a USB port, IR port, RS232 port, or other port), or other communications interface. Software and data transferred via communications interface 624 might typically be carried on signals, which can be electronic, electromagnetic (which includes optical) or other signals capable of being exchanged by a given communications interface 624. These signals might be provided to communications interface 624 via a channel 628. This channel 628 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 608, storage unit 620, media 614, and channel 628. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing system 600 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and embodiments, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various elements of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Although the present technology has been described in detail for the purpose of illustration based on what is currently considered to be the most practical and preferred embodiments, it is to be understood that such detail is solely for that purpose and that the technology is not limited to the disclosed embodiments, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system to monitor eyedrop usage, the system comprising:
    an external detection and activation circuit couplable to an external eyedrop dispenser and configured to wirelessly communicate with a wireless biosensor, the external detection and activation circuit comprising:
        a pressure transducer configured to detect a force applied to the external eyedrop dispenser, wherein a signal to activate the wireless biosensor is transmitted in response to detecting the force at, or above, a threshold value, and
    the wireless biosensor insertable into a region of an eyelid, the wireless biosensor comprising:
        a power supply configured to power at least a transceiver and a sensor;
        the transceiver configured to wirelessly receive the signal from the external detection and activation circuit, wherein the transceiver is configured to, in response to wirelessly receiving the signal, activate the power supply to power the sensor for an activation time, and wherein the transceiver is configured to, in response to wirelessly receiving the signal, activate the sensor for the activation time; and
        the sensor configured to detect a chemical change of the eye in response to usage of the external eyedrop dispenser; and
    wherein the wireless biosensor goes into a sleep mode after the activation time, wherein the sleep mode comprises powering off the sensor.

2. The system of claim 1, wherein the region of the eyelid comprises a lower lacrimal punctum of the eyelid.

3. The system of claim 1, wherein the sensor comprises a temperature sensor to detect a change in a temperature to the tears as a result of the eyedrop usage during the activation time.

4. The system of claim 1, wherein the external detection and activation circuit is couplable to a surface of the external eyedrop dispenser using an adhesive side of the external detection and activation circuit.

5. The system of claim 1, wherein the external detection and activation circuit comprises a hydrogel material that is couplable to different types of eyedrop dispensers.

6. The system of claim 1, wherein the external detection and activation circuit comprises:
    a temperature sensor to be thermally coupled to a surface of the external eyedrop dispenser; and
    a fingerprint identification sensor to detect a user's fingerprint to identify which user is using the external eyedrop dispenser.

7. The system of claim 1, wherein the activation time comprises a duration of about five minutes.

8. The system of claim 1, further comprising a display device comprising a display, wherein information indicating the chemical change is displayed on the display.

9. The system of claim 1, wherein the sensor is further configured to detect a physical change, and wherein the physical change comprises a change in temperature to the tears as a result of the eyedrop usage during the activation time.

10. A method comprising:
    coupling an external detection and activation circuit to an external eyedrop dispenser, wherein the external detection and activation circuit is configured to wirelessly communicate with a wireless biosensor, and wherein the external detection and activation circuit comprises:
        a pressure transducer configured to detect a force applied to the external eyedrop dispenser, wherein a signal to activate the wireless biosensor is transmitted in response to detecting the force at, or above, a threshold value, and;
    inserting the wireless biosensor into an eyelid, wherein the wireless biosensor comprises:
        a power supply configured to power at least a transceiver and a sensor;
        the transceiver configured to wirelessly receive the signal from the external detection and activation circuit;
        the sensor configured to detect a chemical change of an eye in response to usage of the external eyedrop dispenser;
    detecting the force at, or above, the threshold value using the pressure transducer;
    wirelessly receiving the signal at the transceiver;
    activating the power supply to power the sensor for an activation time
    activating the sensor for the activation time;
    during the activation time, dispensing eyedrops from the external eyedrop dispenser on a surface of an eye;
    responsive to activating the sensor for the activation time, detecting the chemical change to the eye as the result of the eyedrop usage during the activation time; and
    going into a sleep mode, wherein the sleep mode comprises powering off the sensor.

11. The method of claim 10, wherein the region of the eyelid comprises a lower lacrimal punctum of the eyelid.

12. The method of claim 10, wherein the sensor comprises a glucose sensor to detect a change in a glucose concentration of the eye during the activation time.

13. The method of claim 10, wherein the external detection and activation circuit is couplable to a surface of the external eyedrop dispenser using an adhesive side of the external detection and activation circuit.

14. The method of claim 10, wherein the external detection and activation circuit comprises a hydrogel material that is couplable to different types of external eyedrop dispensers.

15. The method of claim 10, wherein the chemical change comprises a change in glucose concentration of the eye during the activation time.

16. The method of claim 10, wherein the external detection and activation circuit comprises:
   a temperature sensor thermally couplable to a surface of the external eyedrop dispenser; and
   a fingerprint identification sensor to detect a user's fingerprint to identify which user is using the external eyedrop dispenser.

17. The method of claim 10, wherein the external detection and activation circuit activates the wireless biosensor based on a force applied to at least a portion of the external detection and activation circuit.

18. The method of claim 10, wherein the activation time comprises a duration of about five minutes.

19. The method of claim 10, further comprising: transmitting information indicating the chemical change to a display device, wherein the display device comprises a display; and displaying the information indicating the chemical change on the display of the display device.

20. A system to monitor eyedrop usage, the system comprising: a wireless biosensor insertable into a region of an eyelid, wherein the wireless biosensor comprises:
   a power supply configured to power at least a transceiver and a sensor;
   the sensor configured to detect a chemical change of an eye in response to usage of an external eyedrop dispenser; and
   the transceiver configured to receive a signal from a n external detection and activation circuit, wherein the transceiver is configured to, in response to receiving the signal, activate the power supply to power the sensor for an activation time, and wherein the transceiver is configured to, in response to wirelessly receiving the signal, activate the sensor for the activation time, wherein the external detection and activation circuit, coupled to an external eyedrop dispenser, comprises a pressure transducer detecting a force applied to the external eyedrop dispenser, wherein the signal to activate the wireless biosensor is transmitted upon detecting the force at, or above, a threshold value; and
   wherein the wireless biosensor goes into a sleep mode after the activation time, wherein the sleep mode comprises powering off the sensor.

* * * * *